United States Patent [19]

Laufe et al.

[11] 4,267,839
[45] May 19, 1981

[54] SURGICAL INSTRUMENT FOR USE IN REVERSIBLE STERILIZATION OR PERMANENT OCCLUSION PROCEDURES

[75] Inventors: Leonard E. Laufe, Chapel Hill; Robert G. Wheeler, Durham, both of N.C.

[73] Assignee: Repromed, Inc., Chapel Hill, N.C.

[21] Appl. No.: 74,884

[22] Filed: Sep. 12, 1979

[51] Int. Cl.³ .............................................. A61B 17/12
[52] U.S. Cl. .................................. 128/303 A; 128/326
[58] Field of Search .................. 128/303 A, 326, 305, 128/321, 303 R, 354, 132 R; 29/235

[56] References Cited

U.S. PATENT DOCUMENTS

| 2,137,710 | 11/1938 | Anderson | 128/321 |
| 3,382,873 | 5/1968 | Banich et al. | 128/326 |
| 4,034,473 | 7/1977 | May | 128/305 X |

OTHER PUBLICATIONS

"The Fimbrial Prosthesis" by Leonard Laufe (12-1977) pp. 220-223.

Primary Examiner—Robert W. Michell
Assistant Examiner—Michael H. Thaler
Attorney, Agent, or Firm—B. B. Olive

[57] ABSTRACT

A forcep-like instrument is provided for mounting and ejecting either an elastic band or a hood for an occlusion procedure.

4 Claims, 8 Drawing Figures

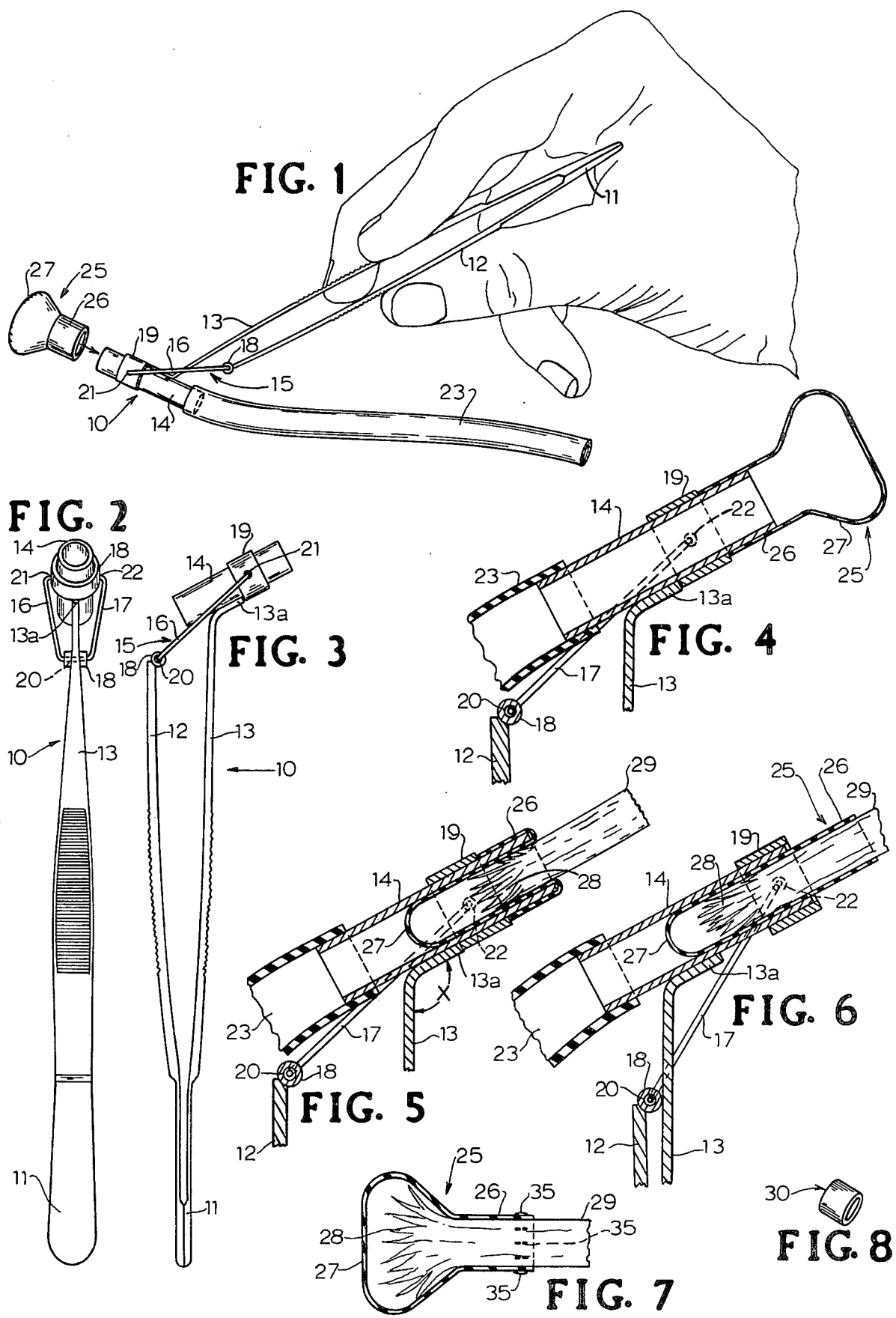

SURGICAL INSTRUMENT FOR USE IN REVERSIBLE STERILIZATION OR PERMANENT OCCLUSION PROCEDURES

BACKGROUND OF THE INVENTION

1. Field of the Invention

The invention relates to medical or surgical instruments and particularly to instruments for use in female sterilization or occlusion procedures.

2. Description of the Prior Art

In the field of female sterilization, it is well known to provide permanent occlusion of the fallopian tube. More recently, the concept of using a fimbrial prosthesis for temporary or reversible female sterilization has been introduced. Capping the fimbria for sterilization involves the utilization of an inert device to protect the fimbria. U.S. Pat. No. 4,050,488 relates to use of fimbrial caps as a method of reversible sterilization.

A paper entitled "The Fimbrial Prosthesis" was presented at a workshop held in San Francisco, Dec. 4-6, 1977, and gives further background and research in the area of reversible female sterilization.

It is to this method of sterilization that the present invention instrument is directed. More specifically, the invention aims to provide an improved instrument for installing bands or hoods in occlusion procedures.

SUMMARY OF THE INVENTION

A forcep-like instrument is provided for mounting and ejecting either an elastic band or a hood for an occlusion procedure. One resilient leg of the device mounts a hollow open ended tube into which the fallopian tube or polypoid structure is drawn. The other somewhat shorter resilient leg is connected by a linkage to a collar which slides on the tube and ejects the band or hood for occluding the fallopian tube or polypoid structure.

DESCRIPTION OF THE DRAWINGS

FIG. 1 is a pictorial view of the instrument of the present invention being held by the operator and with a fimbrial hood about to be placed on the instrument prior to its application to the patient.

FIG. 2 is a front elevation view of the instrument of the present invention.

FIG. 3 is a side elevation view of the instrument of FIG. 2.

FIG. 4 is an enlarged, fragmentary section view through the hood mounting and ejection mechanism with a fimbrial hood of a type employed with the present invention instrument in place.

FIG. 5 is a view similar to FIG. 4 but with the fimbrial hood having been inverted and drawn into the hood mounting sleeve and with the fimbria of the fallopian tube of the patient being delivered into the fimbrial hood.

FIG. 6 is a view similar to that of FIGS. 4 and 5 but with the ejection mechanism activated forcing the fimbrial hood from its mounting sleeve onto the fallopian tube of the patient.

FIG. 7 is a section view through the fimbrial hood after it is put into place and the instrument withdrawn allowing the fimbrial hood to encompass the fimbria and allowing movement of the fimbria within the hood preparatory to anchoring the hood in place with permanent sutures.

FIG. 8 is a pictorial view of an elastomeric, silastic band of the type employed with the instrument of the present invention when permanent occlusion of any tubular or polypoid structure is desired.

DESCRIPTION OF THE PREFERRED EMBODIMENT

Turning now to the drawings, instrument 10 of the present invention is composed of a forcep body 11 having a pair of resilient legs 12, 13 secured to and extending from body 11; an open ended tubular sleeve member 14 integrally secured to a leg extension 13a; a linkage spring 15 having a pair of legs 16, 17; linkage mount 18; and ejection collar 19.

Sleeve member 14 is integrally secured to leg extension 13a which is set at a predetermined angle "X" (FIG. 5) appropriate to use of the instrument and is shown as approximately 120°. Leg 13 is slightly longer in length than leg 12 so that sleeve 14 resides outwardly from the free end of leg 12. A mount 18 is integrally secured to the outer free end of leg 12 and comprises a small sleeve having a bore 20 extending throughout its length. Linkage spring 15 is formed so that it passes through mount 18 by way of bore 20 and its legs 16, 17 extend outwardly and at their outer ends are bent inwardly to resiliently engage ejection collar 19 and provide a pivotal connection.

Ejection collar 19 is designed to be slidably received by sleeve member 14. Collar 19 moves freely on sleeve member 14 between extension 13a which acts as a stop and the outer end of travel on sleeve member 14. A pair of holes 21, 22 are formed in the walls of collar 19 and receive the ends of legs 16, 17 so that collar 19 is retained on sleeve member 14. In a relaxed position, collar 19 rests against leg extension 13a and prevents any movement past this position. When leg 12 is forced toward leg 13 by the fingers of the operator, mount 18 abuts against leg 13 and spring legs 16, 17 force collar 19 forward on sleeve member 14 to the hood or band ejection position seen in FIG. 6.

Turning now to a description of the operation of instrument 10, instrument 10 as shown in FIGS. 1-6 receives a vacuum line 23 which is slidably mounted on the rear end of sleeve member 14. With ejection collar 19 in a retracted position, see FIGS. 1-3, a fimbrial hood 25 is placed on the forward, free end of sleeve member 14, see FIG. 4. In order to do this, shoulder 26 must be stretched over the free end of sleeve member 14 as best seen in FIG. 4. Once in position, shoulder 26 abuts against collar 19. Next, through application of vacuum through vacuum line 23, hood 25 is inverted to the position of FIG. 5. Sometimes, in addition to vacuum, hood 25 must be urged inward by the operator nudging hood 25 with some instrument at hand. Once hood 25 is in position adjacent fimbria 28 as in FIG. 5, fimbria 28 of fallopian tube 29 is guided into hood 25, see FIG. 5. Once fimbria 28 is positioned within hood 25, leg 12 is depressed causing spring legs 16, 17 and correspondingly collar 19 to move forward until shoulder 26 of hood 25 is forced from sleeve member 14 and engages fallopian tube 29. At this point, instrument 10 is withdrawn allowing hood 25 to regain its form as illustrated in FIG. 7. Hood 25 is now anchored in place on tube 29 by placing a sufficient number of sutures 35 through shoulder 26 and into tube 29.

Another application of instrument 10, although not illustrated, would be for situations where permanent occlusion is desired. Such permanent occlusion may be desired for permanent sterilization, permanent occlusion of blood vessels or permanent occlusion of polyps. In this application, an elastomeric, silastic band 30 as illustrated in FIG. 8 is employed and mounted on sleeve 14 and is ejected in the same manner as previously described with respect to hood 25.

The fact that the central axis of the longer leg member 13 resides at an obtuse angle with respect to the central axis of the sleeve member provides a convenient working arrangement. Also, the natural resiliency of the leg members 12, 13 is used to always bring the collar 19 to its retracted position. Thus, the invention instrument may be used rapidly and efficiently in an occlusion procedure.

What is claimed is:

1. An instrument for use in reversible or permanent occlusion procedures, comprising:
   (a) a forcep-like structure providing a pair of resilient leg members of unequal length joined at one end and extending outwardly therefrom in a normally spaced relation;
   (b) a hollow, thin wall, cylindrical, rigid sleeve integrally secured at a position intermediate the length thereof to the terminal end of the longer of said leg members, said sleeve having its central axis oriented at an obtuse angle with respect to the central axis of said longer leg member and having a forward portion extending outwardly from the terminal end of said longer leg member and a rearwardly extending portion positioned to clear said shorter leg member when closed against said longer leg member, the outside diameter of said sleeve being adapted to receive an occluding hood, band device or the like;
   (c) a collar slidably mounted on said forward sleeve portion forward of the terminal end of said longer leg member; and
   (d) a linkage extending between and having pivotal connections to the terminal end of said shorter leg member and said collar enabling said collar to be advanced on and within the length of the forward portion of said sleeve by closing said shorter leg member on said longer leg member and to be retracted by allowing said shorter leg member to retract to its normal outwardly spaced position thereby enabling an occluding device to be installed on and ejected from said sleeve forward portion at appropriate times during the performing of an occlusion procedure.

2. An instrument as claimed in claim 1 wherein the terminal end of the longer of said leg members is bent at said obtuse angle and provides a rearward stop for said collar.

3. An instrument as claimed in claim 2 wherein said shorter leg member when in its normally outwardly spaced position is adapted to retain said collar in its retracted position against the terminal end of said longer leg member.

4. An instrument as claimed in claim 1 wherein the length and outer diameter of said sleeve forward portion are adapted to receive the mounting portion of a fimbrial hood forward of said collar when retracted and the travel of said collar is adapted to eject said mounting portion.

* * * * *

UNITED STATES PATENT AND TRADEMARK OFFICE
CERTIFICATE OF CORRECTION

PATENT NO. : 4,267,839
DATED : May 19, 1981
INVENTOR(S) : Leonard E. Laufe & Robert G. Wheeler It is certified that error appears in the above—identified patent and that said Letters Patent is hereby corrected as shown below:

Col. 1, line 18, "4,050,488" should read --4,050,448--.

Signed and Sealed this

Twenty-first Day of July 1981

[SEAL]

Attest:

GERALD J. MOSSINGHOFF

Attesting Officer

Commissioner of Patents and Trademarks